United States Patent [19]

Besnard et al.

[11] Patent Number: 5,221,790
[45] Date of Patent: Jun. 22, 1993

[54] MIXED POLYSACCHARIDE PRECIPITATING AGENTS AND INSULATING ARTICLES SHAPED THEREFROM

[75] Inventors: Marie-Madeleine Besnard, Antony; Claire David; Magali Knipper, both of Paris, all of France

[73] Assignee: Rhone-Poulenc Chimie, Courbevoie, France

[21] Appl. No.: 737,714

[22] Filed: Jul. 30, 1991

[30] Foreign Application Priority Data

Jul. 30, 1990 [FR] France .................. 90 09669

[51] Int. Cl.[5] .................. C08L 5/00; C12P 19/04; F16L 59/02
[52] U.S. Cl. .................. 536/123; 536/56; 536/84; 536/91; 536/95; 536/96; 536/102; 536/114; 162/100; 106/162; 106/163.1; 106/170; 210/510.1; 210/729; 428/221; 428/532
[58] Field of Search .................. 536/114, 123, 56, 84, 536/91, 95, 96, 102; 210/729, 510.1; 428/221, 532; 162/100; 106/162, 163.1, 170

[56] References Cited

U.S. PATENT DOCUMENTS

| | | | |
|---|---|---|---|
| 3,406,114 | 10/1968 | Goren | 210/730 |
| 4,304,906 | 12/1981 | Kang et al. | 536/114 |
| 4,306,535 | 1/1982 | Majewicz | 536/114 |
| 4,529,797 | 7/1985 | Peik et al. | 536/114 |
| 4,746,528 | 5/1988 | Prest et al. | 536/114 |
| 4,983,563 | 1/1991 | Chopin et al. | 502/150 |
| 4,996,197 | 2/1991 | Mazuel | 536/123 |
| 5,079,348 | 1/1992 | Clare et al. | 536/123 |

FOREIGN PATENT DOCUMENTS

| | | |
|---|---|---|
| 0013217 | 7/1980 | European Pat. Off. . |
| 0291646 | 11/1988 | European Pat. Off. . |
| 1297048 | 6/1969 | Fed. Rep. of Germany . |
| 2058812 | 4/1981 | United Kingdom . |

*Primary Examiner*—Ronald W. Griffin
*Attorney, Agent, or Firm*—Burns, Doane, Swecker & Mathis

[57] ABSTRACT

Mixed polysaccharide compositions, well adopted for flocculating/precipitating solid particulates from liquid dispersions thereof and for the shaping of insulating articles therefrom, comprise (i) at least one polysaccharide prepared by microbial fermentation, the basic recurring structural unit of which comprising both glucose and rhamnose moieties, and (ii) at least one cationic natural polysaccharide or derivative thereof.

30 Claims, No Drawings

MIXED POLYSACCHARIDE PRECIPITATING AGENTS AND INSULATING ARTICLES SHAPED THEREFROM

CROSS-REFERENCE TO COMPANION APPLICATION

Our copending application Serial No. 07/737,766, filed Jul. 30, 1991.

BACKGROUND OF THE INVENTION

1. Field of the Invention

The present invention relates to novel compositions/precipitating agents comprising a polysaccharide produced by microbial fermentation and a natural polysaccharide or derivative thereof, as well as to insulating shaped articles fabricated therefrom.

2. Description of the Prior Art

Polysaccharides whose basic structural unit contains glucose and rhamnose moieties are well known to this art. They are typically prepared by fermentation of a carbon source by means of a microorganism.

Such polysaccharides and processes for the preparation thereof have been described, in particular, in published European Patent Applications No. 77,680 and No. 339,445, and in published French Patent Application No. 88/09,999.

These polysaccharides may be employed for thickening aqueous solutions and for stabilizing, or maintaining in suspension, aqueous dispersions of particles.

Furthermore, polysaccharides of natural origin are also known to this art, as are derivatives of these polysaccharides, prepared, for example, by the semi-synthetic route, and which may also be used for thickening, stabilizing or maintaining suspensions.

These natural polysaccharides are generally obtained from plants such as algae, from roots, seeds or tubers.

It has now surprisingly been found that compositions comprising such polysaccharides behave differently or even, in certain instances, in opposite manner, than as would be expected.

SUMMARY OF THE INVENTION

Accordingly, a major object of the present invention is the provision of novel compositions of matter comprising at least one polysaccharide prepared by microbial fermentation, the recurring structural units of which contain both glucose and rhamnose moieties, as well as at least one natural polysaccharide or derivative thereof.

DETAILED DESCRIPTION OF THE PREFERRED EMBODIMENTS OF THE INVENTION

More particularly according to the present invention, such polysaccharides prepared by microbial fermentation typically contain glucose and rhamnose in molar ratios ranging from 1/1 to 6/1, respectively, preferably from 1/1 to 4/1.

In addition, the basic structural unit of said polysaccharides prepared by microbial fermentation may contain organic acid residues, such as acetyl or pyruvyl residues, as well as other sugars such as glucuronic acid, galactose, mannose, arabinose, fucose or ribose.

The molar ratio between each of said organic acid residues and glucose may range from 1/1 to 0/6, respectively, preferably from 0.5/1 to 0/6.

The molar ratio between each of the other sugars and glucose may range from 2/1 to 0/6, preferably from 1/1 to 0/6.

The polysaccharides prepared by microbial fermentation according to the present invention may be produced, in particular, by fermentation of at least one carbon source contained in a nutrient medium, by means of a microorganism which may belong to the Pseudomonas genus, preferably the species *Pseudomonas paucimobilis* and more preferably the strain I-886 deposited at the CNCM and the strain DSM 4429, to the Alcaligenes genus, preferably the strain Alcaligenes ATCC 31961. The nutrient medium comprising the carbon source, the nature of the carbon source, as well as the preparative processes of such polysaccharides are well described in the literature; compare, in particular, published European Patent Applications No. 77,680 and No. 339,445, as well as published French Patent Application No. 88/09,999, which also describe polysaccharides prepared by microbial fermentation.

The natural polysaccharides and derivatives thereof according to the present invention may be of animal or plant origin. Advantageously, such polysaccharides are gums. By "gums" are intended compounds which, together with water, provide colloidal solutions precipitable by an alcohol such as methanol, ethanol or isopropanol.

Polysaccharides of animal origin may be obtained from the carapace of certain animals such as crustacea, like chitin. Natural polysaccharides of plant origin may be obtained from algae, seeds, roots or tubers. Exemplary thereof are galactomannans such as guar gum, carob gum, tara gum, cassia gum, glucomannans such as konjakmannan, alginates, in particular sodium alginate, gum acacia, gum arabic, agar or the various starches. The preferred natural polysaccharides comprise the alginates.

Exemplary natural polysaccharide derivatives include the chitin derivatives such as chitosan, cellulose semi-synthetic derivatives such as hydroxymethylcellulose, hydroxymethylpropylcellulose, hydroxyethylcellulose or hydroxypropylcellulose. Also exemplary are starch and galactomannan cationic derivatives, in particular cationic guar. Such cationic derivatives are well known to this art and are typically available commercially. They are generally prepared by etherification of esterification of the free hydroxyl groups of the sugars which constitute the natural polysaccharide, by means of quaternary ammonium organic compounds such as 2,3-epoxymethylammonium chloride.

The natural polysaccharides or derivatives thereof according to the present invention have a molecular weight which is typically greater than 200,000, generally ranging from 200,000 to 3,000,000.

According to this invention, the weight ratios between the polysaccharide prepared by microbial fermentation and the natural polysaccharide or derivative thereof range from 5/95 to 95/5, preferably from 30/70 to 70/30.

In addition to the polysaccharides described above, the composition according to the invention may comprise a flocculating additive.

By "flocculating additive" is intended a compound which permits or enhances the formation of flocs during the suspension, in aqueous solution, of said polysaccharides prepared by microbial fermentation and said natural polysaccharides or derivatives thereof.

Exemplary such flocculating additives include quaternary ammonium organic compounds, ammonium hydroxide, synthetic anionic organic polymers or copolymers and their salts, as well as compounds based on a metal of the iron and/or aluminum group, such as aluminum and/or iron sulfate, chloride, hydroxychloride or chlorosulfate.

Particularly representative quaternary ammonium compounds are n-alkyltrimethylammonium, n-dialkyldimethylammonium, n-alkyldimethylammonium, n-alkylpyridinium and benzalkonium salts. In these compounds, the alkyl moiety advantageously has 1 to 30, preferably 8 to 24 carbon atoms.

Such anionic organic polymers or copolymers may be based on acrylic acid or methacrylic acid such as polyacrylic acid and polymethacrylic acid.

The weight of flocculating agent contained in the compositions of the invention typically ranges from 0.0001% to 0.03% of the total weight of the polysaccharides prepared by microbial fermentation and said natural polysaccharides or derivatives thereof.

The compositions according to the invention may be formulated by simple mixing of the constituent polysaccharides prepared as a powder, or by mixing one of said powdered polysaccharides into an aqueous solution comprising the other polysaccharide.

Preferably, the polysaccharide prepared by microbial fermentation and the natural polysaccharide or, separately, one of its derivatives, may also be suspended in solution and then the two solutions obtained mixed with stirring. The stirring must be adequate in order to obtain a homogeneous solution. The flocculating additive may be added at any time in one or the other of the said solutions, but preferably in said homogeneous solution. The latter may comprise 0.001% to 0.3% by weight, preferably 0.002% to 0.6% by weight of the compositions of the invention.

The present invention also features a process for precipitating, in an aqueous medium, a dispersion of solid particles by means of the above compositions.

Such particles may be of organic or inorganic nature and of various sizes. Their concentration in the aqueous medium wherein they are dispersed is variable. It should be appreciated that such a precipitative effect of the compositions of the invention is unexpected and surprising, given that it is known to this art that the polysaccharides prepared by microbial fermentation and natural polysaccharides or derivatives thereof are typically used as suspending agents.

It is necessary, however, in order to attain a good precipitation, for the concentration of the compositions according to the invention in the aqueous medium to range from 0.001% to 0.5%, preferably from 0.005% to 0.2% by weight.

During such process, the compositions according to the invention may be mixed with said dispersion, for example in the form of a homogeneous solution such as described above.

The process described above may be used, in particular, for treating waste waters which comprise solid particles in suspension and which are flocculated and then precipitated.

This process may also be used for the preparation of insulating shaped articles and materials based on mineral fibers and comprising the compositions of the invention.

Such shaped articles/materials may be provided in the form of panels or plates which can withstand very high temperatures. They may therefore be used for protection against fire, as refractory insulating material for thermal ovens and combustion chambers or even as acoustic insulating material.

In addition to such mineral or inorganic fibers and a composition according to the invention, these insulating shaped articles may also comprise at least one mineral filler material.

Exemplary such mineral fibers include boron fibers, carbon fibers, glass fibers and ceramic fibers such as alumina, silica-alumina fibers and silica-alumina fibers modified by other oxides such as chromium, boron, zirconium, calcium and magnesium oxides, titanium dioxide, silicon carbide, silicon nitride, carbonitride and boron nitride fibers, as well as fibers of mineral wools such as diabase wool, rock wool or slag wool. These fibers advantageously have a length of 0.1 to 50 mm and a diameter of 1 to 20 microns.

Exemplary fillers which comprise the composition of the insulating shaped article may include silicas such as colloidal silicas, aluminas, bentonite, magnesia, calcium carbonate, kaolin or aluminum silicates.

The insulating shaped articles according to the invention may be produced from an aqueous dispersion of mineral fibers which may optionally comprise the mineral filler with which the composition according to the invention is mixed, such that its concentration by weight in the dispersion is as indicated above.

Such a dispersion may comprise 1% to 10%, preferably 4% to 6% by weight of dry solids.

The mixture of the dispersion and the composition according to the invention causes precipitation of the fibers and, optionally, of the dispersed mineral fillers.

The solids materials may then be separated from the supernatant aqueous phase by a physical separation process, for example by filtration. Thereafter, said solid materials may be conditioned, dried and optionally baked. The conditioning is carried out according to conventional technique as a function of the intended ultimate use of the insulating shaped article.

After drying, the latter usually comprises 30% to 90% by weight of mineral fibers, optionally, 5% to 60% by weight of mineral fillers, and 0.5% to 7%, preferably 1% to 5% by weight of a composition according to the invention.

The insulating shaped articles comprising a composition according to the invention exhibit enhanced mechanical properties relative to the known insulating materials. But, in particular, by means of such composition, it is possible to considerably reduce the proportion of organic materials contained in the insulating shaped article. However, too high an amount of organic material presents numerous disadvantages, in particular, the emission of a black smoke during baking of the insulating shaped article.

Utilizing a composition according to the invention, it is also possible to manufacture items based on wood fibers, in particular via a process similar to that employed for manufacturing said insulating shaped articles described above. According to one process, the mineral fibers are replaced by wood fibers.

In order to further illustrate the present invention and the advantages thereof, the following specific example is given, it being understood that same is intended only as illustrative and in nowise limitative.

EXAMPLE 100 g of a solution of polysaccharides were prepared by mixing 22 g of a 0.5% by weight solution of a polysaccharide prepared by fermentation by means of a *Pseudomonas paucimobilis* I-886 strain with 22 g of a 1% by weight cationic guar solution and 56 g of drinking water.

The polysaccharide prepared by means of said *Pseudomonas paucimobilis* I-886 strain, as well as a process for the preparation thereof, are described in French Patent Application No. 88/09,999.

The cationic guar used was that marketed by Meyhall under the trademark Meyproid 9806.

22 g of alumina-silica ceramic fibers were dispersed in 2,100 g of water in a 5-liter beaker with stirring at 500 revolutions/min. The solution of polysaccharides was then introduced into this dispersion while maintaining the stirring.

After two minutes, the stirring was stopped. The fibers precipitated. The precipitated fibers were separated from the aqueous solution by filtration under vacuum in a Buchner funnel. The filter cake was dried.

The insulating shaped article thus produced contained 1.5% by weight of polysaccharides relative to the weight of fibers.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A mixed polysaccharide composition of matter, comprising (i) at least one polysaccharide prepared by microbial fermentation, the basic recurring structural unit of which comprises glucose and rhamnose moieties, and (ii) at least one cationic natural polysaccharide or derivative thereof.

2. The mixed polysaccharide as defined by claim 1, said at least one polysaccharide prepared by microbial fermentation comprising glucose and rhamnose moieties in molar ratios of from 1/1 to 6/1, respectively.

3. The mixed polysaccharide composition as defined by claim 2, said molar ratios ranging from 1/1 to 4/1, respectively.

4. The mixed polysaccharide composition as defined by claim 1, said at least one polysaccharide prepared by microbial fermentation further comprising organic acid and/or other sugar moieties.

5. The mixed polysaccharide composition as defined by claim 4, said at least one polysaccharide prepared by microbial fermentation further comprising acetyl or pyruvyl moieties, and/or glucuronic acid, galactose, mannose, arabinose, fucose or ribose moieties.

6. The mixed polysaccharide composition as defined by claim 1, said at least one polysaccharide (i) having been prepared by Pseudomonas or Alcaligenes fermentation of a nutrient medium comprising at least one carbon source.

7. The mixed polysaccharide composition as defined by claim 6, said at least one polysaccharide (i) having been prepared by *Pseudomonas paucimobilis* fermentation.

8. The mixed polysaccharide composition as defined by claim 7, said at least one polysaccharide (i) having been prepared by Pseudomonas paucimobilis I-886 DSM 4429 fermentation.

9. The mixed polysaccharide composition as defined by claim 6, said at least one polysaccharide (i) having been prepared by Alcaligenes ATCC 31961 fermentation.

10. The mixed polysaccharide composition as defined by claim 1, comprising at least one plant or animal polysaccharide (ii) or derivative thereof.

11. The mixed polysaccharide composition as defined by claim 10, said at least one plant or animal polysaccharide (ii) or derivative thereof comprising a gum.

12. The mixed polysaccharide composition as defined by claim 10, comprising a cellulose derivative.

13. The mixed polysaccharide composition as defined by claim 12, said cellulose derivative comprising hydroxymethylcellulose, hydroxyethylcellulose, hydroxymethylpropylcellulose or hydroxypropylcellulose.

14. The mixed polysaccharide composition as defined by claim 10, comprising a cationic starch or galactomannan.

15. The mixed polysaccharide composition as defined by claim i, wherein the weight ratio between the at least one polysaccharide prepared by microbial fermentation and the at least one natural polysaccharide or derivative thereof ranges from 5/95 to 95/5.

16. The mixed polysaccharide composition as defined by claim 15, said weight ratio ranging from 30/70 to 70/30.

17. The mixed polysaccharide composition as defined by claim 1, further comprising a flocculating agent.

18. The mixed polysaccharide composition as defined by claim 17, said flocculating agent comprising a quaternary ammonium organic compound, ammonium hydroxide, a synthetic anionic organic polymer or copolymer or salt thereof, or an iron or aluminum group compound.

19. An aqueous solution comprising the mixed polysaccharide composition as defined by claim 1.

20. In a process for precipitating solid particulates from an aqueous dispersion thereof by adding an effective amount of a precipitating agent thereto, the improvement which comprises utilizing as such precipitating agent the mixed polysaccharide composition as defined by claim 1.

21. The process as defined by claim 20, comprising adding such mixed polysaccharide precipitating agent to a concentration ranging from 0.001% to 0.5% by weight.

22. The process as defined by claim 21, said concentration ranging from 0.005% to 0.2% by weight.

23. The process as defined by claim 20, said solid particulates comprising inorganic fibers.

24. The process as defined by claim 23, said solid particulates also comprising inorganic filler material.

25. The process as defined by claim 20, said solid particulates comprising wood fibers.

26. An insulating shaped article, comprising an insulating amount of inorganic fibers and the mixed polysaccharide composition as defined by claim 1.

27. The insulating shaped article as defined by claim 26, further comprising at least one inorganic filler material.

28. An insulating shaped article, comprising an insulating amount of wood fibers and the mixed polysaccharide composition as defined by claim 1.

29. The insulating shaped article as defined by claim 28, further comprising at least one inorganic filler material.

30. In a process for the purification of a water supply having particulate impurities suspended therein by flocculating/precipitating such impurities therefrom, the improvement which comprises flocculating/precipitating such impurities with the mixed polysaccharide composition as defined by claim 1.

* * * * *